United States Patent
Shelton

(12) 
(10) Patent No.: US 6,561,382 B2
(45) Date of Patent: May 13, 2003

(54) METHOD AND APPARATUS FOR DISINFECTING A WATER COOLER RESERVOIR AND ITS DISPENSING SPIGOT(S)

(75) Inventor: James J. Shelton, Ponchatoula, LA (US)

(73) Assignee: S.I.P. Technologies, L.L.C., Mandeville, LA (US)

( * ) Notice: Subject to any disclaimer, the term of this patent is extended or adjusted under 35 U.S.C. 154(b) by 0 days.

(21) Appl. No.: 09/881,796

(22) Filed: Jun. 15, 2001

(65) Prior Publication Data

US 2003/0000966 A1 Jan. 2, 2003

(51) Int. Cl.⁷ .............................. C02F 1/78; B67D 5/58
(52) U.S. Cl. .................... 222/1; 222/185.1; 222/190; 210/760
(58) Field of Search ................. 222/185.1, 190; 426/236; 210/749, 758, 760

(56) References Cited

U.S. PATENT DOCUMENTS

| | | | |
|---|---|---|---|
| 3,448,045 A | 6/1969 | Hess et al. | |
| 3,692,180 A | 9/1972 | Laraus | |
| 3,726,404 A | 4/1973 | Troglione | |
| 4,019,986 A | 4/1977 | Burris et al. | |
| 4,805,808 A | * 2/1989 | Larson | 215/383 |
| 4,842,723 A | 6/1989 | Parks et al. | |
| 5,015,394 A | 5/1991 | McEllhenney et al. | |
| 5,295,519 A | 3/1994 | Baker et al. | |
| 5,328,059 A | 7/1994 | Campbell | |
| 5,366,619 A | 11/1994 | Matsui et al. | |
| 5,531,908 A | 7/1996 | Matsumoto et al. | |
| 5,567,332 A | 10/1996 | Mehta | |
| 5,582,717 A | 12/1996 | Disanto | |
| 5,587,089 A | 12/1996 | Vogel et al. | |
| 5,669,221 A | 9/1997 | Lebleau et al. | |
| 6,085,540 A | 7/2000 | Davis | |
| 6,149,804 A | * 11/2000 | Chung et al. | 210/192 |
| 6,289,690 B1 | * 9/2001 | Davis | 210/760 |
| 6,361,686 B1 | * 3/2002 | Conrad | 210/120 |

FOREIGN PATENT DOCUMENTS

| | | |
|---|---|---|
| EP | 0163750 A | 12/1984 |
| EP | 0739312 B1 | 1/1999 |
| GB | 2022979 | 12/1979 |
| JP | 361103595 A | 5/1986 |
| WO | WO88/04279 | 6/1988 |
| WO | WO92/04969 | 4/1992 |
| WO | WO93/17725 | 9/1993 |
| WO | WO97/42924 | 11/1997 |

* cited by examiner

*Primary Examiner*—Gene Mancene
*Assistant Examiner*—Stephanie L. Willatt
(74) *Attorney, Agent, or Firm*—Garvey, Smith, Nehrbass & Doody, LLC; Stephen R. Doody; Charles C. Garvey, Jr.

(57) ABSTRACT

A method and apparatus for providing sanitized water in a bottled water dispenser includes a reservoir and one or more dispensing spigots. An ozone generating system generates ozone for sanitizing the water. Ozone is generated and collected within an ozone generator housing. A blower transmits air to the housing, the air carrying the ozone through flowlines to an air diffuser that is positioned inside the reservoir of the water dispenser. The flowlines can be used to sanitize one or more of the reservoir, spigot(s), and/or channel that connects the reservoir and spigot(s). A return flowline or lines can return ozone from the spigot to one or both of the channel and/or reservoir for further use in sanitization.

36 Claims, 10 Drawing Sheets

METHOD AND APPARATUS FOR DISINFECTING A WATER COOLER RESERVOIR AND ITS DISPENSING SPIGOT(S)

CROSS-REFERENCE TO RELATED APPLICATIONS

Not applicable

REFERENCE TO A "MICROFICHE APPENDIX"

Not applicable

BACKGROUND

The present invention relates to bottled water dispensers, and more particularly to an improved bottled water dispenser for dispensing water that has been sanitized using ozone. More particularly, the present invention relates to an improved method and apparatus for sanitizing a water cooler reservoir, its dispensing spigots, and the flow channel that connects the reservoir and spigot(s).

One of the most common types of commercially available bottled water dispensers is a floor standing cabinet having an open top that receives a large inverted bottle. The bottle is typically of a plastic or glass material having a constricted neck. The bottle is turned upside down and placed on the top of the cabinet with the neck of the bottle extending into a water filled reservoir. The water seeks its own level in the reservoir during use.

The cabinet provides one or more spigots for dispensing water, typically one being for cooled water, one being for ambient temperature water, and optionally a hot water spigot can be provided. As a user draws water from a spigot dispenser, the liquid level in the reservoir drops until it falls below the neck of the bottle at which time water flows from the bottle and bubbles enter the bottle until pressure has equalized.

These types of inverted bottle water dispensers are sold by a number of companies in the United States. Many are refrigerated. Some have heating elements. There are other types of water dispensers that employ a cabinet with spigots. Some receive water directly from a piped source. Others pump water from a contained water bottle or source that is hidden inside the cabinet.

One of the problems with bottled water dispensers such as the inverted bottle type is that of cleansing the unit from time to time. Because the top is not air tight, it "breathes" so that bacteria can easily enter the reservoir over a period of time.

Five gallon bottles that are typically used in combination with a cabinet are also a source of bacteria and germs. Most of these bottles are transported on trucks where the bottles are exposed to outside air. They are handled by operators that typically grab the bottle at the neck, the very part of the bottle that communicates with a water reservoir during use. Unfortunately, it is difficult to convince every person that handles these bottles to wash their hands frequently enough.

In order to properly sanitize such a water dispenser or cooler, the user must carefully clean the neck of the bottle prior to combining the bottle with the cabinet. Further, the user should drain and sanitize the reservoir from time to time. The cleansing of the reservoir in such a water dispenser is a time consuming project that is typically not done often enough. The spigots are also in need of sanitization as they are often contacted by unsanitary drinking containers, human hands and children's mouths.

SUMMARY

The present invention provides an improved, self sanitizing water dispenser apparatus as well as a method for generating ozone for cleaning the reservoir and the water contained within it.

The present invention provides a self sanitizing bottled water dispenser that includes a cabinet holding a supply bottle of water to be dispensed. In some embodiments, water is pumped to the reservoir from the supply bottle. In other embodiments, water is piped directly to the reservoir from a water pipe system. Spigots on the cabinet dispense the water. A reservoir can receive flow from the supply bottle.

The bottle contains water to be dispensed, and provides a neck portion and a dispensing outlet portion.

A reservoir contained within the cabinet next to the upper end portion thereof contains water with a water surface that communicates with a bottle neck during use. Spigots dispense cold, ambient and/or hot water. A refrigeration system cools the water within the reservoir. A diffuser (eg. ring diffuser) emits bubbles into the reservoir, the diffuser being disposed within the reservoir at the lower end portion thereof. The diffuser can be placed next to the reservoir wall so that bubbles emitted by the diffuser help scrub the wall.

An ozone generator module is supported within the housing. Air flow lines communicate with an air pump to carry ozone from the ozone generator housing to the diffuser. A blower can be provided to generate air flow, and a flow line connects the blower to the ozone generator housing.

A timer can be provided for activating the ozone generator at a selected time and for a selected time interval. The ozone generator is activated for a selected time interval (e.g. a few minutes). After the selected time interval, the ozone generator is shut off.

The diffuser is preferably positioned around the side of the reservoir at the bottom of the reservoir, close to the intersection of the reservoir bottom wall and reservoir side wall.

The diffuser can be preferably circular in shape, and can have a composite construction that includes a porous core that is partially covered with a non-porous coating.

A preferred embodiment provides a dispenser with water cooler spigot(s) capable of both being automatically sanitized with ozone as well as providing a means for sanitizing the water channel between the reservoir and the spigot.

The ozone generating module cleanses and sanitizes the water cooler reservoir.

Two additional areas within the water cooler can be addressed by the method and apparatus of the present invention to completely sanitize water dispenser/cooler. The first is the water channel, comprised of the watercourse within the spigot itself, lying behind the spigot valve and the remaining watercourse between the spigot and the cooler reservoir. The second area is the spigot portion which is ahead of the valve. This spigot portion is the inside of the spigot dispenser tip that is alternately exposed to water, air, unsanitary drinking containers, children's mouths and occasional fingers.

In one embodiment the integration of two ozone gas supply sanitation channels into a spigot or faucet with associated connectors and components is disclosed. The first ozone channel addresses the water channel. This first ozone channel is open to the water channel, immediately behind the spigot valve and is connected to the primary ozone supply. The ozone gas supply flow stream to the reservoir diffuser can be provided by means of a tee connection outside of the cooler reservoir. Incorporated within this ozone channel of the spigot is a small ozone diffuser stone whose permeability is preferably matched to that of the reservoir diffuser stone ring. This serves to match supply pressure facilitating proper functioning. The internal surface area of the stone's volume is much smaller than that of the diffuser ring, thus insuring that a proportionally smaller amount of ozone gas is transferred to the small volume of water within the water channel. The existing ozone generating module check valve eliminates water from siphoning into the ozone generator.

The second ozone channel can consist of a preferably tangential opening that tangentially intersects the spigot dispenser tip channel to sanitize the spigot tip outlet. Tangential flow creates a downward spiral flow of heavier than air ozone gas that can be used to completely engulf the outlet channel's surface and the valve seat. This channel extends to the air chamber at the top of the water cooler reservoir. The build-up of ozone above the water level within the reservoir has sufficient concentration and pressure to serve as the supply for sanitizing the spigot tip outlet.

Since the spigot tip outlet is exposed to air, with the recycled ozone transferring directly to air, the need for a diffuser is eliminated. The elevation of the orifice eliminates water build-up in the chase after dispensing. Ozone gas is supplied to the spigot only when the ozone generating module is in operation.

BRIEF DESCRIPTION OF THE DRAWINGS

For a further understanding of the nature, objects, and advantages of the present invention, reference should be made to the following detailed description, read in conjunction with the following drawings, wherein like reference numerals denote like elements and wherein.

DETAILED DESCRIPTION OF THE INVENTION

Figure 1:
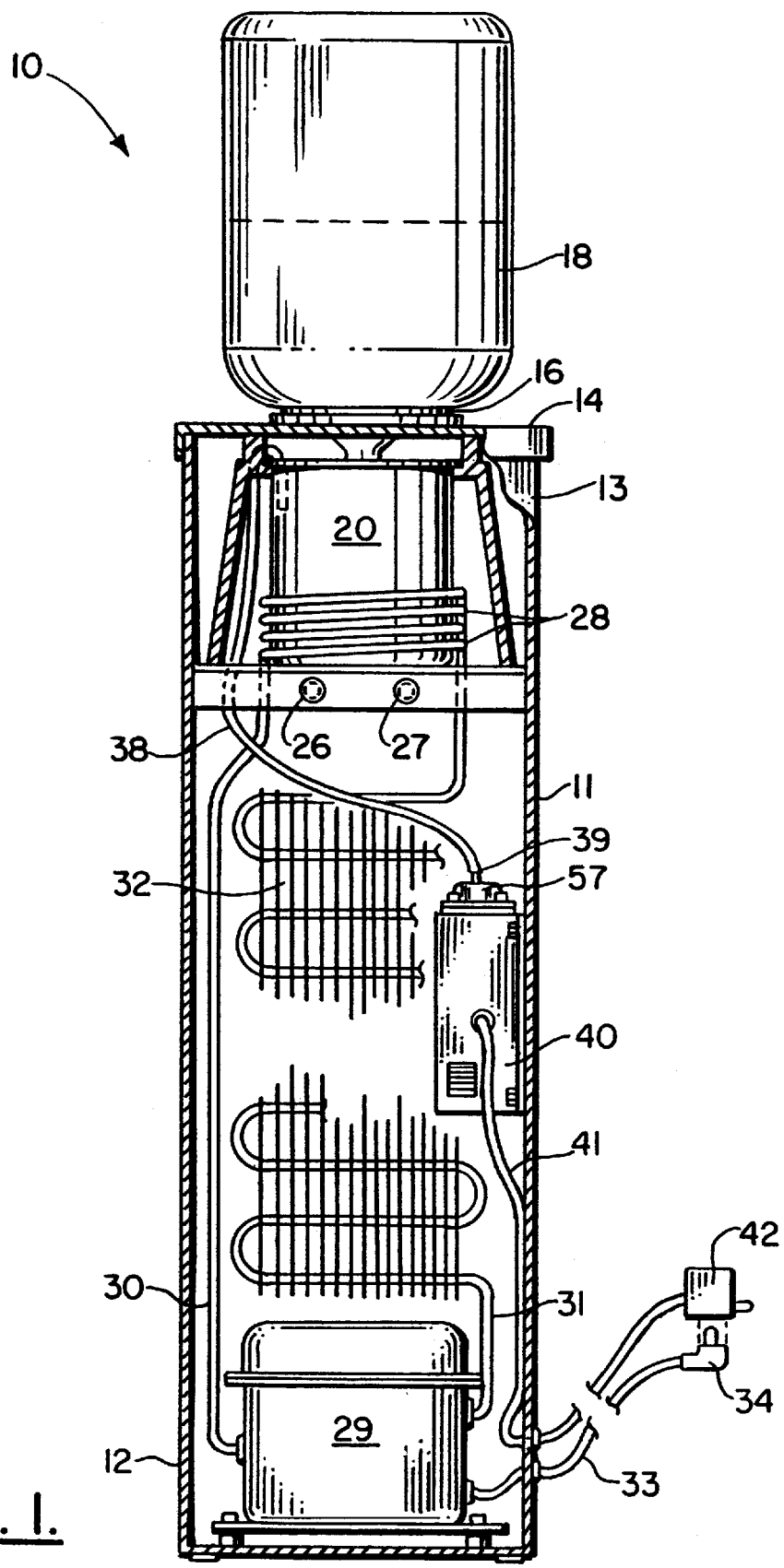
FIG. 1 is a sectional elevational view of the preferred embodiment of the apparatus of the present invention.
Figure 2:
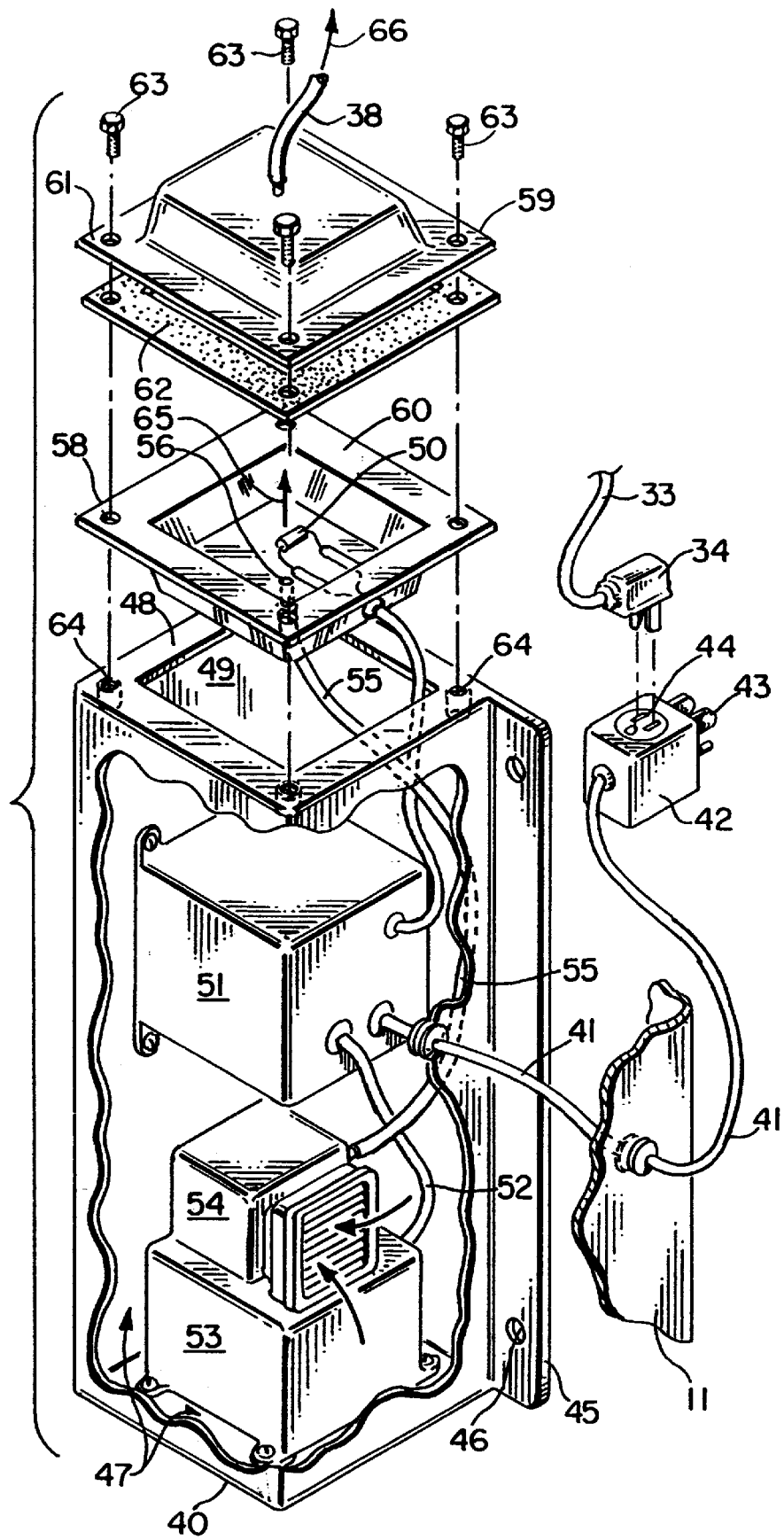
FIG. 2 is a partial perspective exploded view of the preferred embodiment of the apparatus of the present invention illustrating the ozone generator portion thereof.
Figure 3:
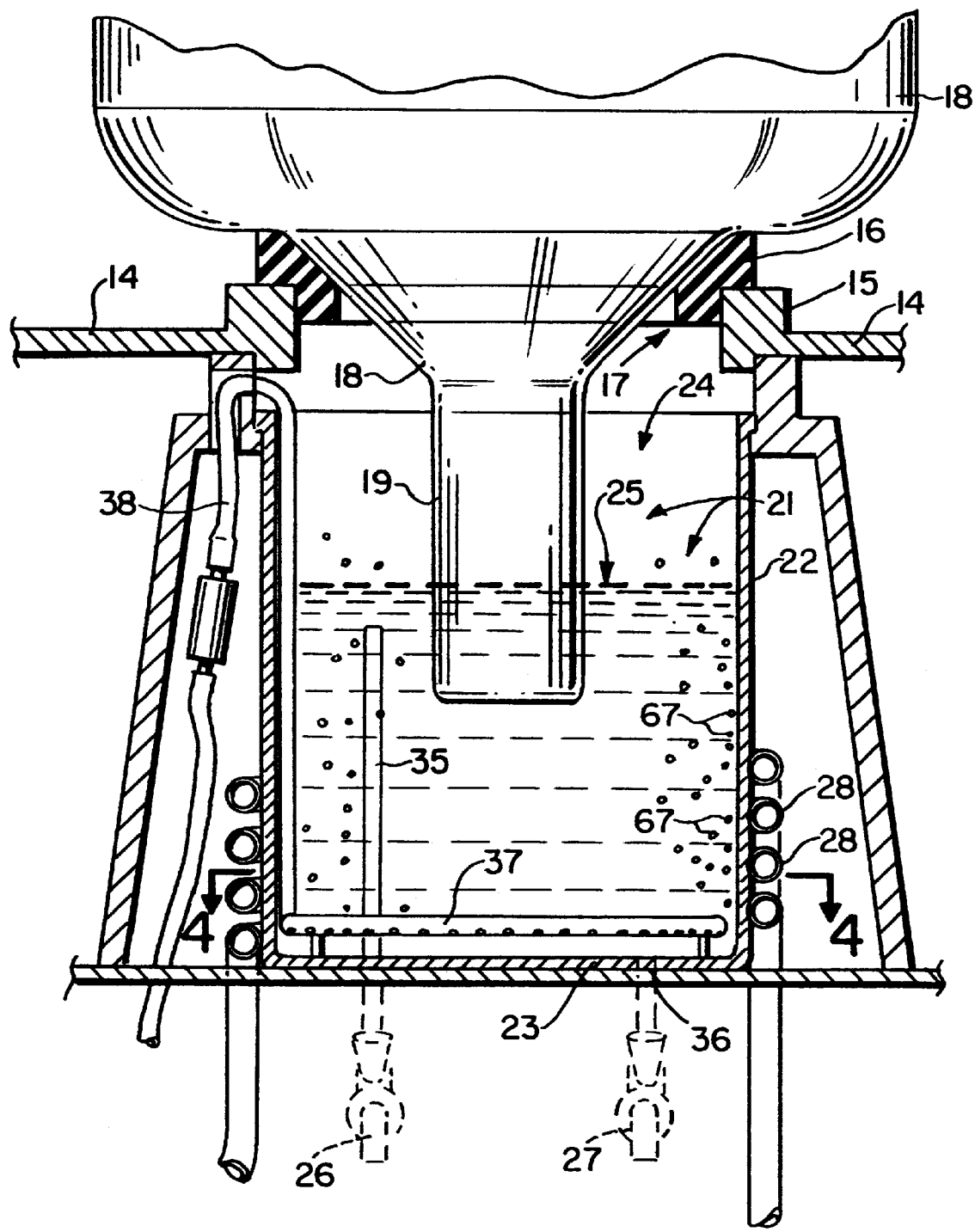
FIG. 3 is a partial sectional elevational view of the preferred embodiment of the apparatus of the present invention illustrating the reservoir, bottle, and ozone diffuser portions thereof.

FIGS. 1–3 show generally the preferred embodiment of the apparatus of the present invention designated by the numeral 10 in FIG. 1. Water dispenser 10 provides an improved apparatus that sanitizes the open reservoir from time to time with ozone. The apparatus 10 includes a cabinet 11 having a lower end portion 12 and an upper end portion 13. The upper end portion 13 carries a cover 14 having an opening 17.

The opening 17 provides an annular flange 15 and a gasket 16 that define an interface between cabinet 11 and bottle 18. The bottle 18 can be any commercially available bottle, typically of a several gallon volume (e.g. five gallons). The bottle 18 provides a constricted bottled neck 19 that is placed inside an open reservoir 20 as shown in FIGS. 1 and 3 during use. The bottle neck 19 has an opening for communicating with a reservoir 20 at the interior of the cabinet 11 that holds the water product to be dispensed and consumed. When the water level 25 in the reservoir 210 is lowered during use, air bubbles enter the bottle 18 and water replenishes the reservoir 20 until pressure equalizes.

The reservoir 20 has an interior 21 surrounded by reservoir sidewall 22 and reservoir bottom wall 23. The reservoir 20 can be, for example, generally cylindrically shaped and of a stainless steel or plastic material. The reservoir 20 provides an open top for communicating with the neck 19 of bottle 18.

During use, reservoir 20 has water surface 25 that fluctuates slightly as water is dispensed and then replenished by bottle 18. One or more spigots 26, 27 can be provided for withdrawing water contained in reservoir 20. In the embodiment shown in FIG. 3, for example, a left hand spigot 26 has a flow line 35 that extends up to and near the surface 25 of water contained in reservoir 20. The spigot 26 thus removes ambient temperature water from reservoir 20 that is not in close proximity to the cooling coils 28. The spigot 27 provides a port 36 for communicating with water contained in reservoir 20. Because the refrigeration coils 28 are positioned at the lower end of reservoir 20, the spigot 26 withdraws cool water. As a practical matter, a water dispenser apparatus 10 could provide either ambient temperature water, cold water or heated water if, for example, a flow line 35 were to be provided with a heating element.

For cooling the water at the lower end portion of the reservoir 20, a cooling system that includes a compressor 29 can be provided. The refrigeration system includes flow lines 30, 31 in combination with compressor 29 to transmit cooling fluid to coils 28 and then to heat exchanger 32 as part of a system for cooling water in reservoir 20. Power to the apparatus 10 is provided by electrical lines, including an electrical line 33 provided with plug 34. The plug 34 can be fitted to controller 42 having receptacle 44 and plug 43 as shown in FIG. 2. In this fashion, electricity can be selectively routed to the compressor 29 via electrical line 33 or to the housing 40 containing ozone generator 50 using electrical line 41. This feature enables the compressor to be deactivated when the ozone generator 50 is to be used to transmit ozone to reservoir 20 for cleaning water contained in it and for scrubbing the inside walls of reservoir 20.

In FIGS. 1 and 2, the housing 40 includes an ozone generator 50 that generates ozone for cleaning water contained in reservoir 20. Additionally, the housing 40 contains a motor drive 53 and blower 54 that move air through an ozone generator housing 57 to diffuser 37. Air line 38 communicates between ozone generator housing 57 and ozone diffuser 37. Fitting 39 provides a connection for attaching the exit air flow line 38 to ozone generator 57 as shown in FIGS. 1 and 2.

Housing 40 can be provided with flanges 45 and openings 46 for enabling the housing 40 to be retrofitted to an existing cabinet 11 by bolting the housing 40 to the cabinet 11 as shown in FIG. 1.

In FIG. 2, housing 40 includes a lower end portion 47 and an upper end portion 48. The upper end portion 48 provides an opening 49 to which ozone generator housing 57 can be affixed. An ozone generator 50 is contained within the housing 57 as shown in FIG. 2. Housing 57 includes a lower housing section 58 and an upper housing section 59. Flange 60 of lower housing section 58 and flange 61 of upper housing section 59 each engage gasket 62 upon assembly.

Bolted connections 63 can be used for attaching the housing 57 to housing 40 at internally threaded openings 64 on housing 40 as shown in FIGS. 1 and 2. During use, the controller 42 normally deactivates the ozone generator 50 during normal hours when the users are dispensing water from the apparatus 10. Because the ozone used to disinfect reservoir 20 has a distinctive smell, it is preferable to clean the water contained in reservoir 20, to clean the inside walls of reservoir 20 and the bottle neck 19, at a selected time. The controller 42 could be activated for example during early morning hours (e.g. 3:00 a.m.–4:00 a.m.) and can be a commercially available controller that activates transformer 51 and motor drive 53 only after compressor 29 and the refrigeration system have been deactivated by the controller 42. This accomplished by shutting off the flow of electricity to plug 34 and electric line 33 that supply electricity to compressor 29.

Figure 4:
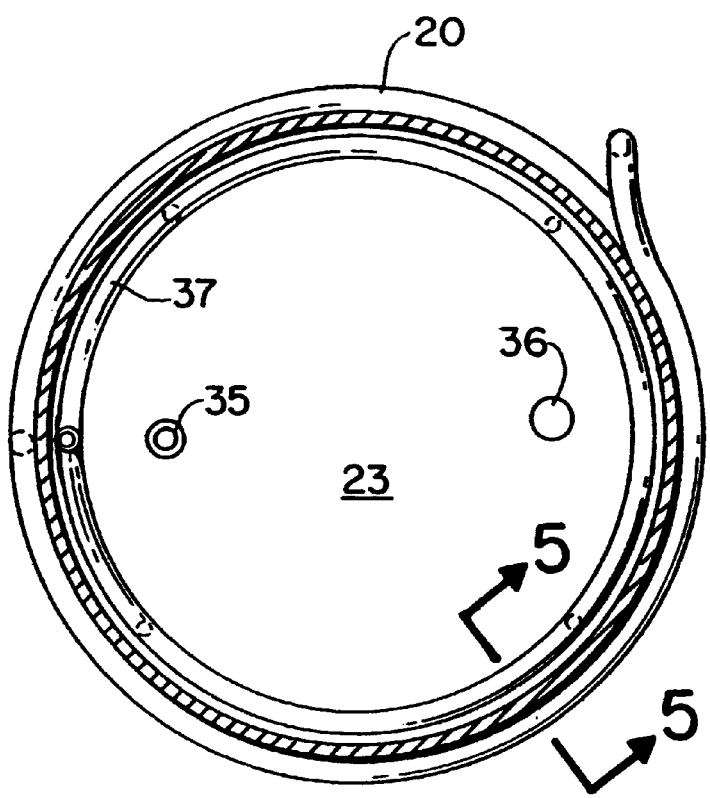
FIG. 4 is a fragmentary view of the preferred embodiment of the apparatus of the present invention illustrating the open reservoir and ozone diffuser.

After electricity is disconnected from compressor 29, transformer 51 and motor drive 53 are activated. The transformer 51 produces electricity with a very high voltage (eg. about 7,000–9,000 VAC range, and ultimately VDC) at ozone generator 50 for generating ozone within the confines of ozone generator housing 57. As this ozone is generated within housing 57, air is pumped with air pump 54 into inlet flow line 55 and via opening 56 into the interior of housing 57. Optional HEPA filter 71 removes airborne microorganism before they can enter air pump 54 and flow line 55. A dryer (eg. silica gel) can also be used to remove humidity. This positive flow of air pressure into housing 57 causes a simultaneous discharge of air through fitting 39 into air flow line 38. The air flow line 38 then carries air to diffuser 37 (FIGS. 7–14) that is contained at the bottom at the side wall of reservoir 20. The specific placement of diffuser 37 and the flow of air therefrom containing ozone is shown more particularly in FIGS. 4–14. In FIG. 4, a top view of the reservoir shows that the diffuser 37 preferably extends 360 degrees about the periphery of reservoir 20 and at the sidewall 22 thereof This is preferable because ozone bubbles 67 are used to scrub the side wall 22 at the inside surface as shown in FIG. 3.

Figure 6:
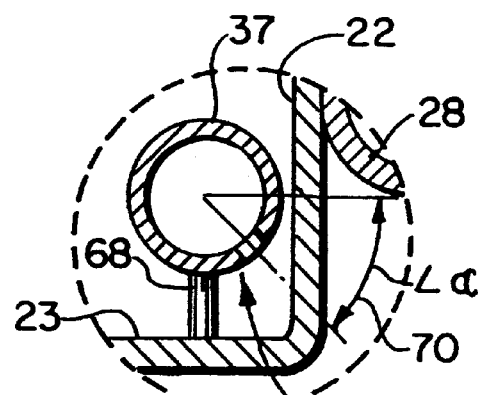
FIG. 6 is a fragmentary elevational view illustrating the ozone diffuser and its position in relation to the reservoir.
Figure 5:
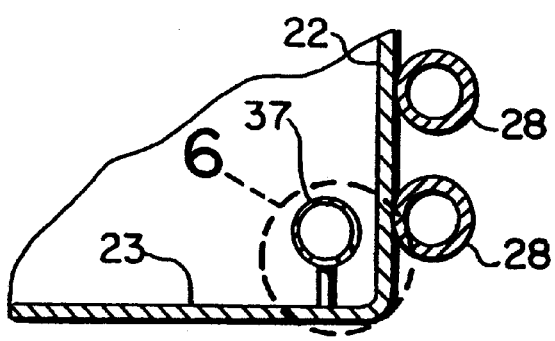
FIG. 5 is a sectional view taken along lines 5—5 of FIG. 4.

The diffuser 37 can be is supported by a plurality of feet 68 that extend between the diffuser 37 and a bottom wall 23 of reservoir 20. Openings 69 in diffuser 37 are directed at an angle with respect to the bottom wall 23 and side wall 22 of reservoir 20 as shown in FIG. 6. An angle 70 of preferably about 45 degrees defines the orientation of openings 69 with respect to the walls 22, 23. This configuration of the openings 69 relative to the walls 22, 23 ensures that bubbles 67 will be discharged outwardly toward side wall 22, to maximize the scrubbing effect at the interior wall 22 of reservoir 20. This scrubbing action using ozone bubbles 67 cleans the sidewall 22 and produces a rolling flow of water within reservoir 20. The bubbles 67 will strike the surface 25 of the reservoir 20 and flow inwardly. Such a circulation ensures that all of the water within the reservoir 20 is cleaned. Further, directing the bubbles from diffuser 37 outwardly toward wall 22 ensures that none of the bubbles 67 will enter bottle 18 via neck 19 which would cause the device to overflow.

Figure 7:
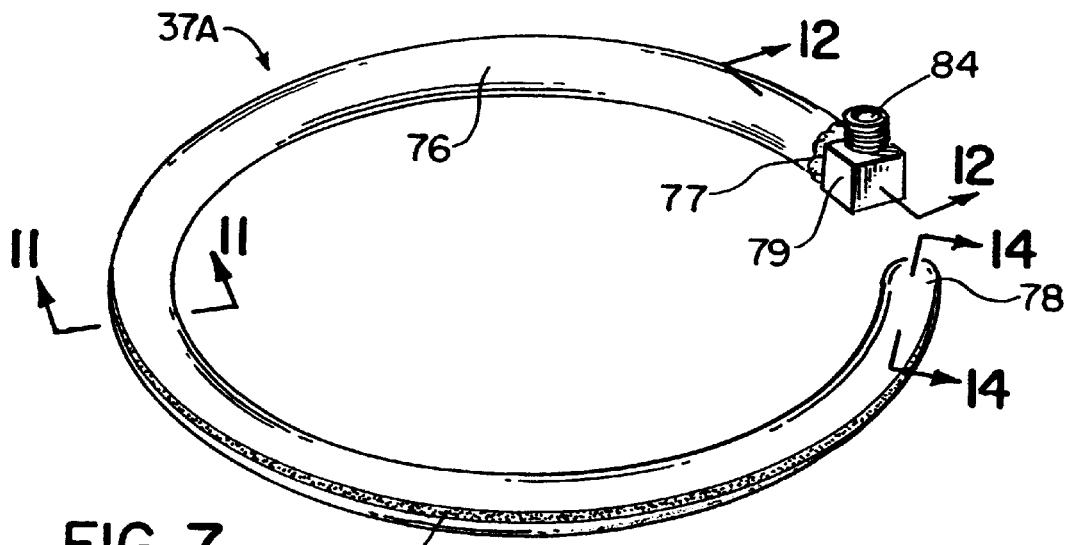
FIG. 7 is a fragmentary view illustrating a preferred construction for the diffuser.
Figures 8, 9, 10:
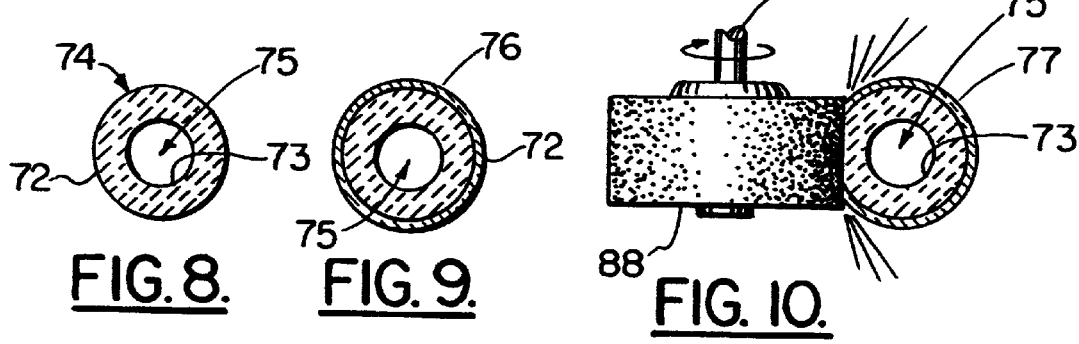
FIG. 8 is a fragmentary, sectional view of the diffuser of FIG. 7 showing only the porous body portion thereof.
FIG. 9 is a fragmentary, sectional view of the diffuser of FIG. 7 prior to a grinding of part of the non-porous surface therefrom.
FIG. 10 is a schematic, fragmentary view illustrating the diffuser of FIG. 7 during construction.

FIGS. 7–14 show an alternate construction of the diffuser, wherein the diffuser is designated generally by the numeral 37. Diffuser 37 has a porous body 72 as shown in FIG. 8 that begins with a cylindrically shaped hollow cross section. Porous body 72 can be a food grade porous ceramic material. The porous body 72 is generally 0 shaped as shown in FIG. 7, but provides the cross section shown in FIG. 11. FIGS. 8, 9 and 10 show the method of construction of the diffuser 37 which begins with porous body 72. In FIG. 8, porous body 72 has an inner surface 73 that surrounds hollow bore 75 and an outer surface 74. In FIG. 9, a non-porous coating (e.g. food grade non-porous ceramic that can be fired) is provided on porous body 72 to provide an outer coating 76 that is substantially impervious to the escape of air. In FIG. 10, rotary grinding tool 88 having rotary shaft 89 is used to grind away part of the non-porous coating 76 to provide an exposed face 90 (see FIGS. 10 and 11). Another method of manufacture could be used that masks the area that will generate air bubbles. The non-porous coating 76 is then applied. After application of the non-porous coating, the mask is peeled away to expose face 90 that will generate the air bubbles.

Figures 11, 12:
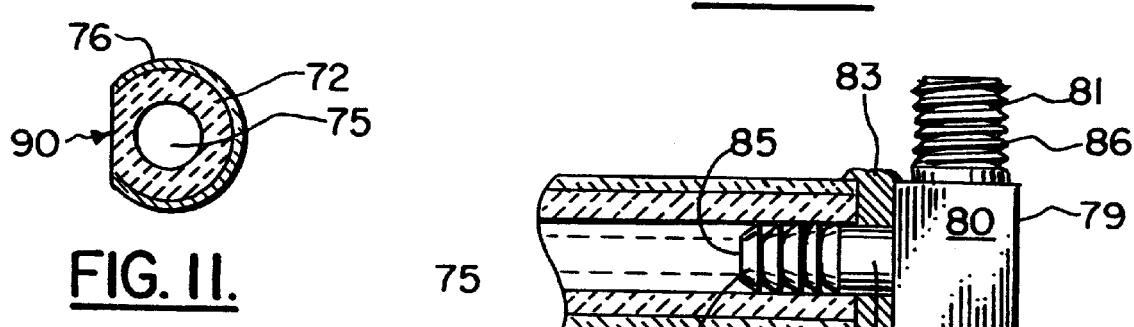
FIG. 11 is a sectional view taken along lines 11—11 of FIG. 7.
FIG. 12 is a sectional view taken along lines 12—12 of FIG. 7.
Figure 13:
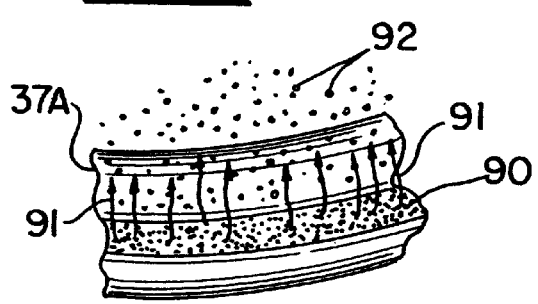
FIG. 13 is a fragmentary, perspective view illustrating the diffuser of FIG. 7.

When air is injected through inlet elbow fitting 79, the air enters hollow bore 75 and then diffuses through porous body 72. Coating 76 prevents the escape of air so that air can only escape through exposed face 90. Exposed face 90 is positioned on the outer portion of 0 shaped diffuser 37 as shown in FIGS. 7 and 11. An enlarged view of this exposed face 90 is shown in FIG. 13 with arrows 91 indicating the escape of bubbles 92.

The inlet elbow fitting 79 has a body 80 with three legs 81, 82, and 82A extending therefrom. Coupling material 83 such as food grade epoxy can be used to join the combination of porous body 72 and its coating 76 to inlet elbow fitting 79.

Figure 14:
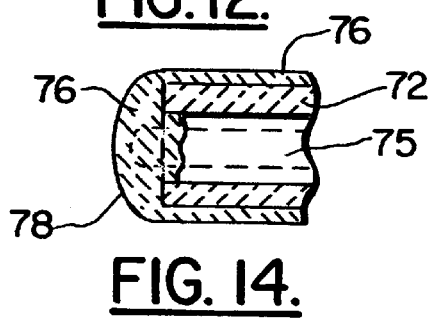
FIG. 14 is a sectional view taken along lines 14—14 of FIG. 7.

Each of the legs 81, 82, and 82A provides an internal hollow flow bore, said bores 84, 85 and 85A intersecting at body 80 so that air flow can proceed from bore 84 of leg 81 to bores 85 of leg 82 and 85A of leg 82A. The leg 81 can provide external threads 86 so that it can be connected to an influent air flow line 38. Other connectors could be used on leg 81 such as a stab fitting type connection, clamp connection or the like. T-fitting 79 at legs 82, 82A can provide similar connective material for forming a connection with porous body 72 at its inner surface 73. This connective structure on legs 82, 82A can be a stab fitting type connection as shown in FIG. 12, external threads, or like connective structure. FIG. 14 shows a longitudinal section through line 14—14 of FIG. 7.

Figure 15:
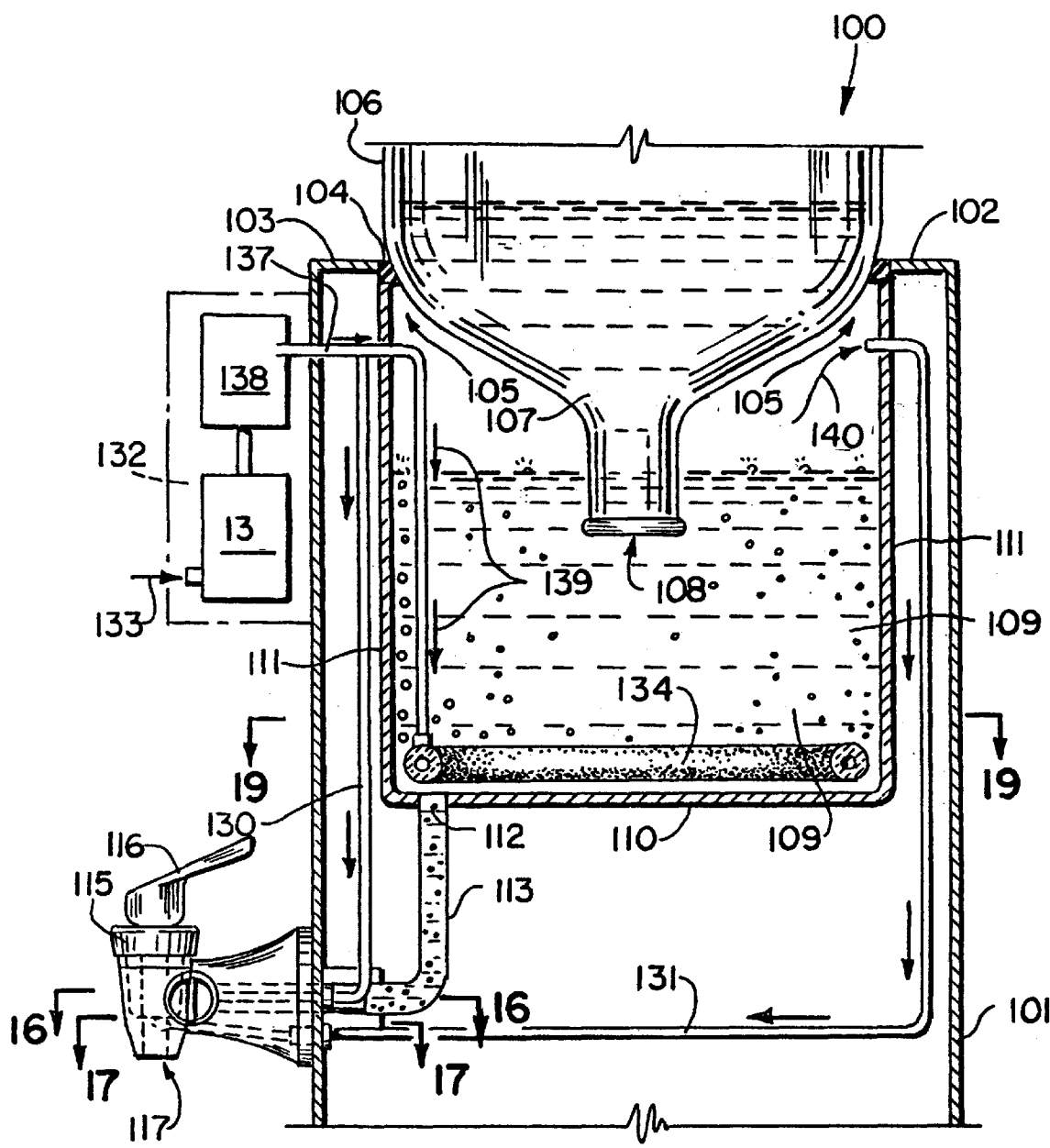
FIG. 15 is a sectional elevation view of a preferred embodiment of the apparatus of the present invention.

FIGS. 15–19 show a preferred embodiment of the apparatus of the present invention designated generally by the numeral 100 in FIG. 15. Water dispenser 100 has a cabinet 101 that can be in the form of an inverted bottle water type cabinet. However, the present invention can be used with other types of cabinets, such as for example, cabinets that contain a bottle of water at the lower end portion of the cabinet, or cabinets that connect directly to a water supply, thus eliminating the supply bottle.

Cabinet 101 has an upper cover portion 102 that includes an annular flange 103 surrounding opening 105. Gasket 104 can be used to form a seal between bottle 106 and cabinet 101.

Bottle 106 has a neck 107 and an opening 108 that communicates with reservoir 109. Reservoir 109 includes a bottom 110 that can be square or circular and side walls 111. An outlet 112 at the bottom 110 of reservoir 109 communicates with flow channel 113. Flow channel 113 has a flow bore 114 for carrying water between reservoir 109 and spigot 115.

Figure 16:
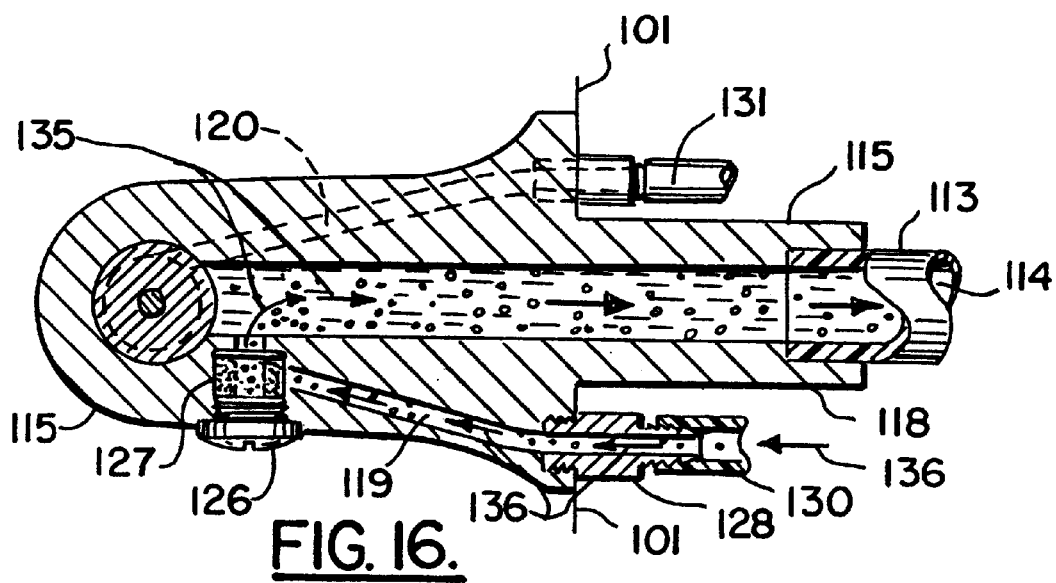
FIG. 16 is a sectional view taken along lines 16—16 of FIG. 15.
Figure 17:
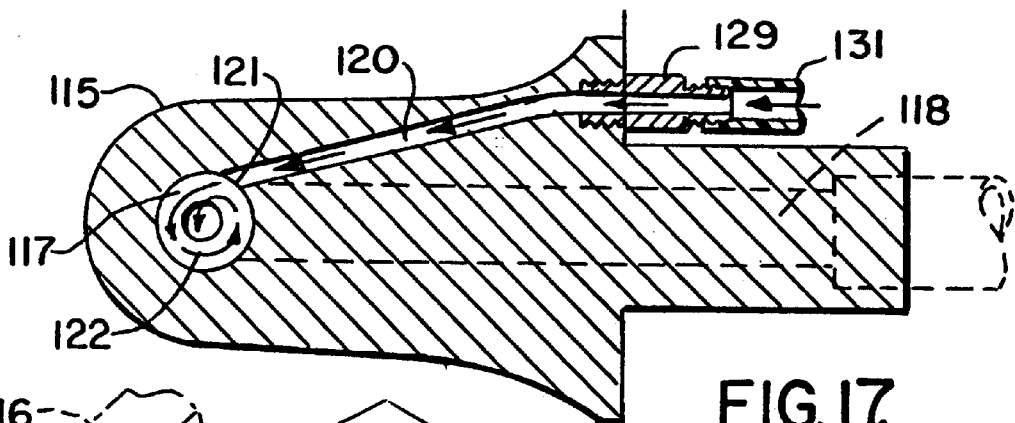
FIG. 17 is a sectional view taken along lines 17—17 of FIG. 15.
Figure 18:
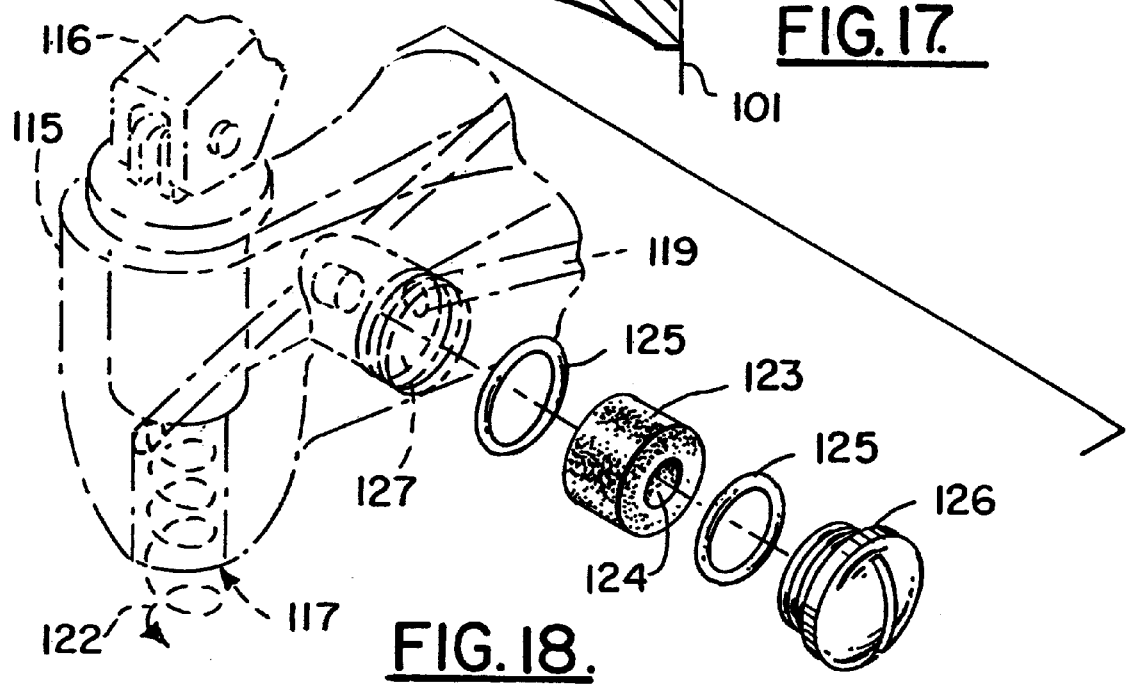
FIG. 18 is a partial perspective view of the alternate embodiment of the apparatus of the present invention.
Figure 19:
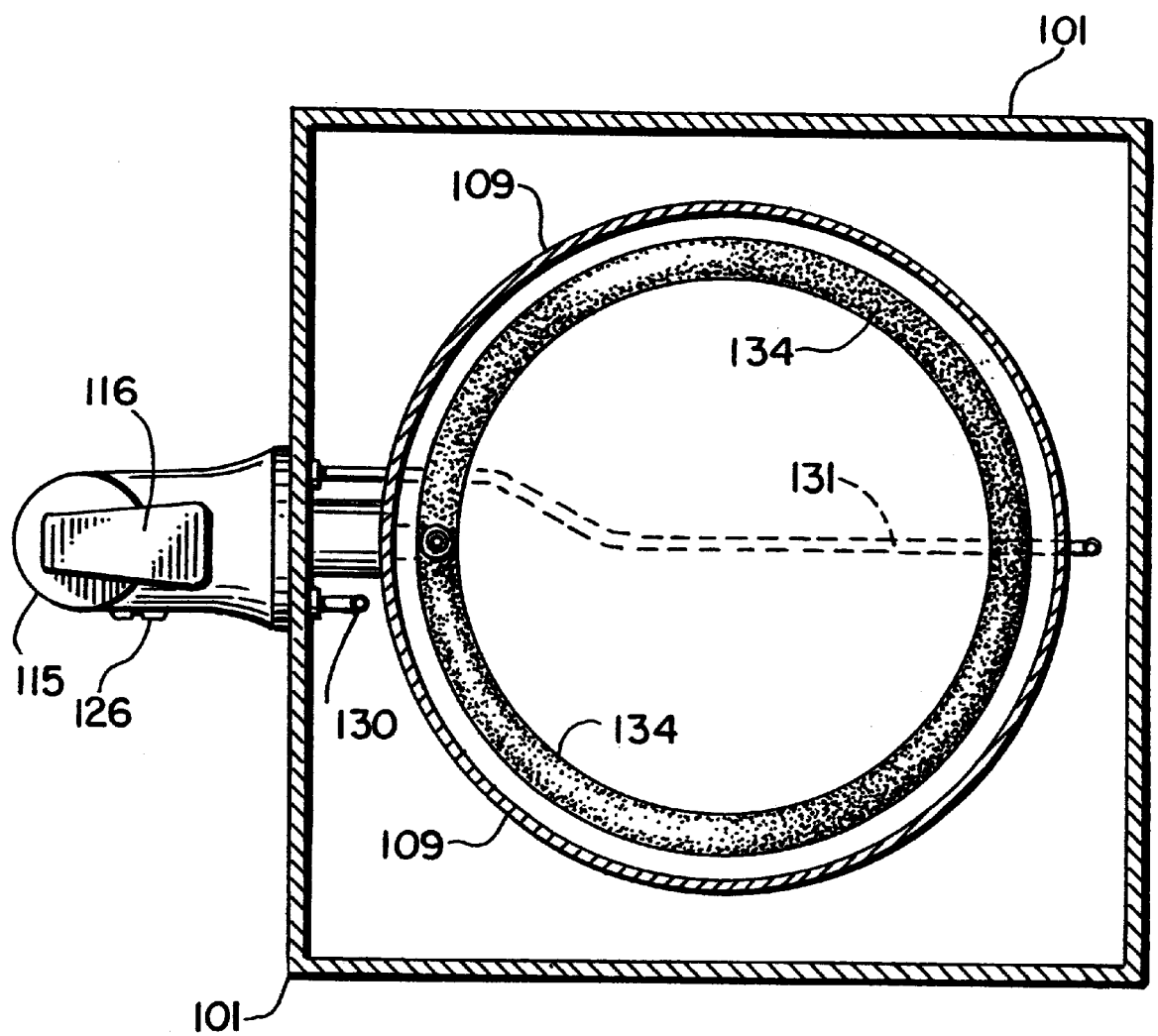
FIG. 19 is a sectional view taken along lines 19—19 of FIG. 15.

In FIGS. 16–18, spigot 115 provides a valve 116 that can be gripped and actuated by a user in order to open dispensing outlet opening 117 so that water flows via opening 117 into a selected glass, cup or like receptacle. Such a valve 116 for actuating a spigot 115 is known in the art.

Spigot flow channel 118 communicates with bore 114 of channel 113. In addition to spigot flow channel 118, there are provided on spigot 115 a pair of passages that extend through spigot 115. These passages include first passage 119 and second passage 120. The first passage 119 extends to an internally threaded opening 127. Opening 127 receives diffuser stone 123 that has an opening 124 through which air can enter opening 127 and then provide small air bubbles to spigot flow channel 118 as indicated by arrows 135 in FIG. 16.

During use, ozone is transmitted via ozone flowline 130 to fitting 128 and then to passageway 119 as indicated by the arrows 136 in FIG. 16. The ozone that flows in line 130 and in passage 119 provides small bubbles of ozone for disinfecting and sanitizing the spigot flow channel 118 and also the flow bore 114 of channel 113. Since the spigot channel is near reservoir walls on most or all cooling water dispensers, it will not contribute to bubbles entering the water bottle and thus dispensing water.

In FIGS. 15 and 16, the bubbles that enter spigot channel 118 can be shown flowing in the direction of arrows 135 in the horizontal section of channel 113 and then to the vertical section of channel 113 in FIG. 15 rising upwardly to outlet 112 and entering reservoir 109. Thus, the same bubbles that are used to sanitize spigot channel 118 and channel 113 also enter and assist in sanitizing reservoir 109.

Reservoir 109 is also sanitized using flowline 137 that extends from ozone generator module 132 to diffuser 134 in the direction of arrows 139 in FIG. 15. The second passage 120 receives ozone from reservoir 109. Ozone flows into ozone flowline 131 that communicates with fitting 129 and second passage 120 as shown in FIG. 17. The ozone flowing in second passage 120 communicates with spigot dispensing opening 117 at tangent position 121. This produces a spiraling flow of ozone within dispensing opening 117 as indicated schematically by the spiraling arrow 122 in FIGS. 17 and 18.

Ozone generator module 132 can be comprised of an ozone generator 138 and airblower 140. Air flow, schematically indicated by the arrow 133 can be provided using a blower for pushing the generated ozone into the flowlines 130, 131 and 137.

Figure 20:
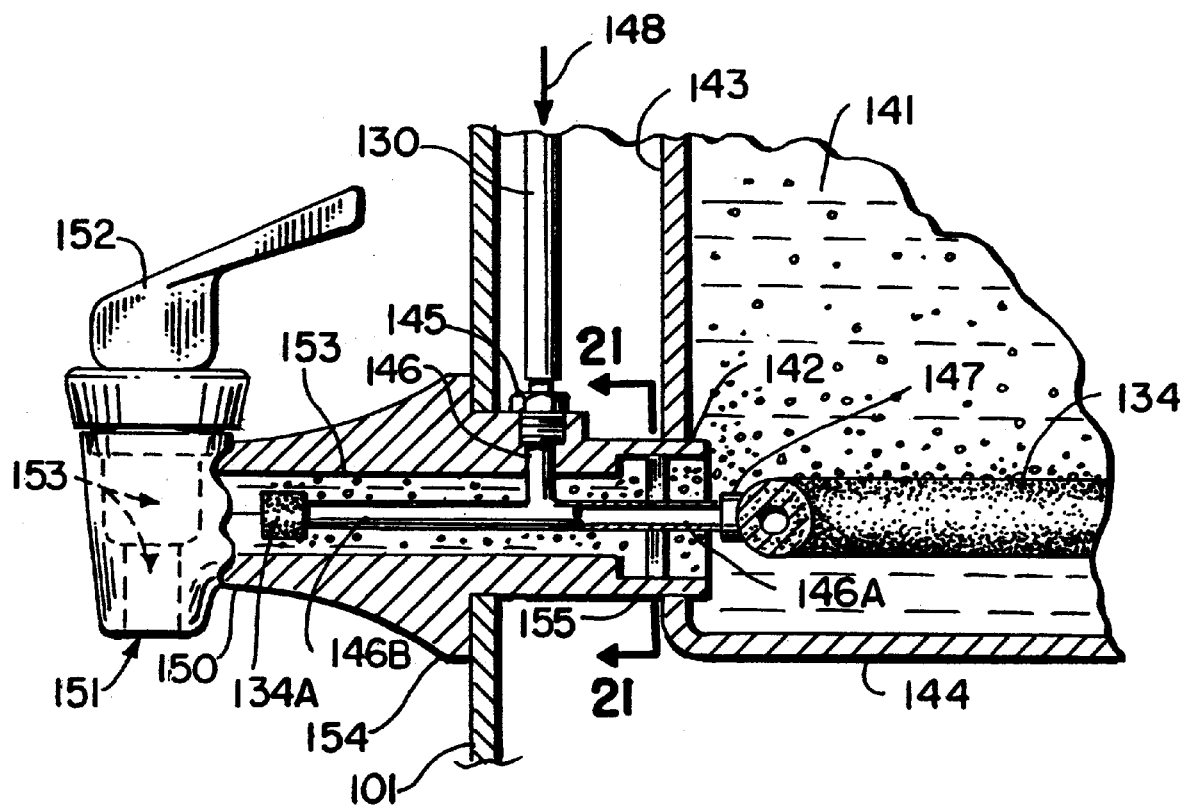
FIG. 20 is a sectional elevation view of the alternate embodiment of the apparatus of the present invention, and showing an alternate construction for the spigot.
Figure 21:
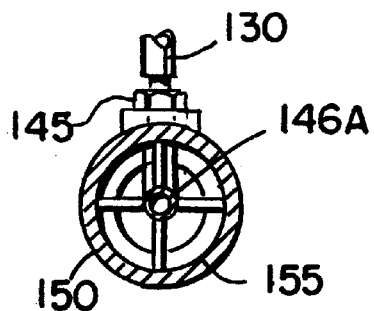
FIG. 21 is a sectional view taken along lines 21—21 of FIG. 20.

In FIGS. 20–23, additional constructions for the spigot and the channels that communicate with the spigot to sanitize it with ozone are shown. In FIG. 20, reservoir 141 includes a sidewall 143 and bottom 144. The reservoir 141 has a single opening 142 that receives a spigot inlet portion 155 of spigot 150. In FIGS. 20 and 21, ozone is transmitted to both the spigot 150 and the reservoir 141 via flowline 130. In FIGS. 20 and 21 flowline 130 receives flow directly from blower 140 and ozone generator 138 and flowline 131 is eliminated. Rather, ozone flows through flowline 130 to flowline 146A to diffuser 134 and to flowline 146B to diffuser 134A.

Spigot 150 includes flowline 146A,B communicating with fitting 145 as shown in FIG. 20. Flowline 146A,B includes a T-portion as shown in FIG. 20 disposed within spigot channel 153. Flowline 146A,B extends between fitting 147 and diffuser 134A. In this fashion, ozone flows from generator 138 via flowline 130 to fitting 145, to flowline 146A, to fitting 147, and then to diffuser 134. Additionally, ozone flows from generator 138 via flowline 130 to fitting 145, to flowline 146B, and then to diffuser 134A. The only opening that is formed in the walls 143, 144 of reservoir 141 is the single opening 142 that receives the spigot inlet portion 155 as shown in FIG. 20.

In order to operate the spigot 150, valve 152 is provided that opens channel 153 so that water can flow from reservoir 141 via channel 153 to outlet opening 15 1. Arrow 148 in FIG. 20 shows the direction of ozone flow in flowline 130 during use. Annular flange 154 of spigot 150 forms an attachment to cabinet 101, being secured in opening 142 using an interference fit, adhesive, or other suitable connection.

Figure 22:
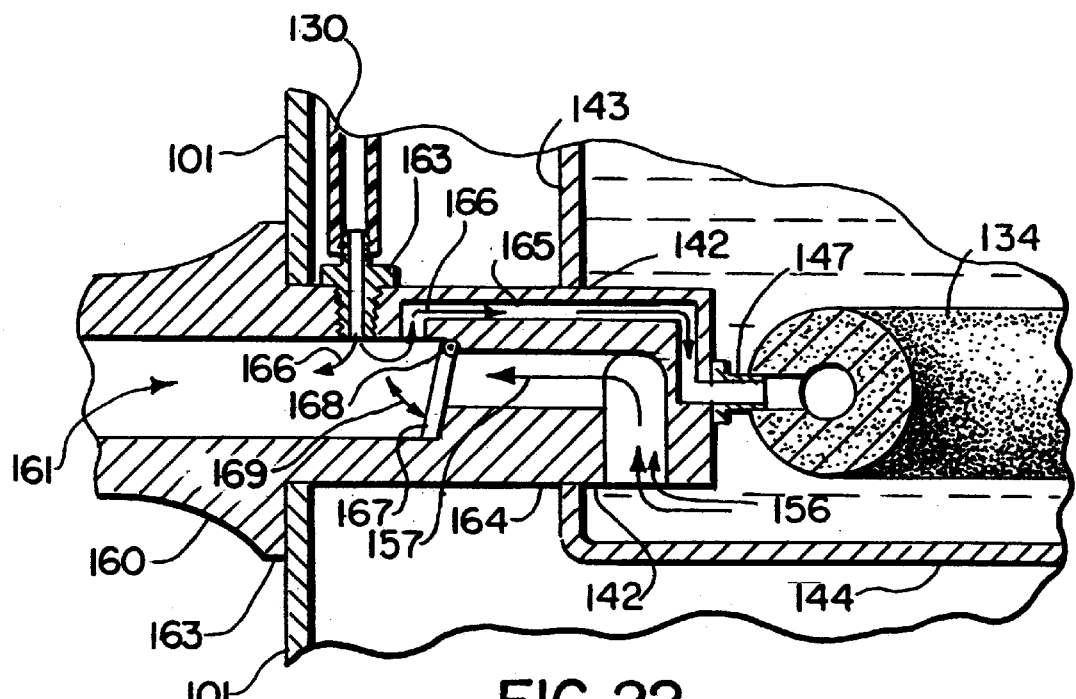
FIG. 22 is a sectional elevation view of the alternate embodiment of the apparatus of the present invention, showing another construction for the spigot.
Figure 23:
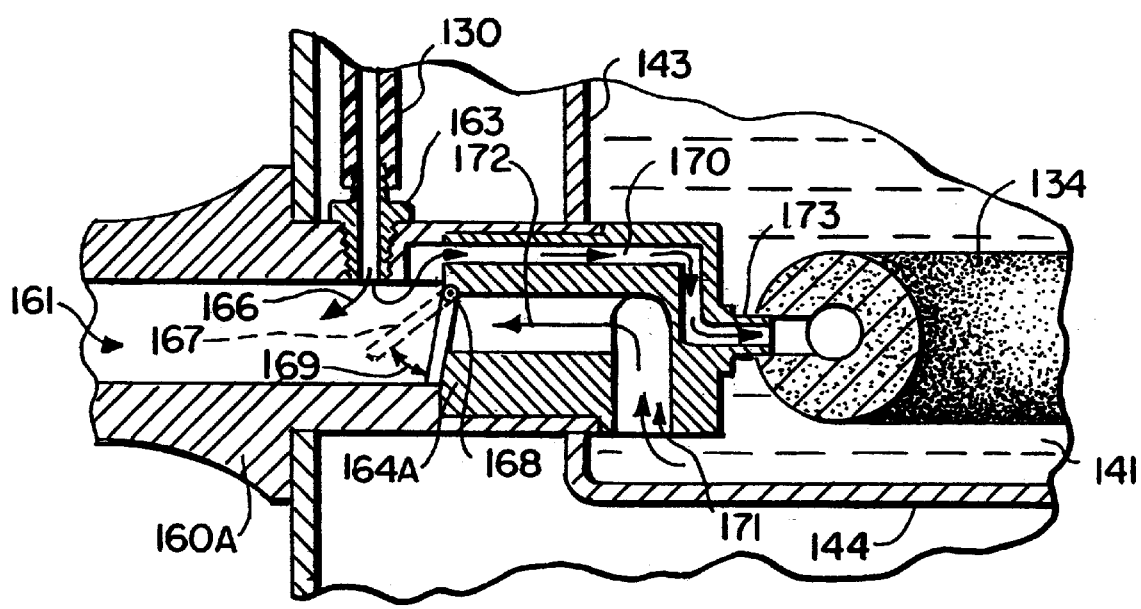
FIG. 23 is a sectional elevation view of the alternate embodiment of the apparatus of the present invention, showing another construction for the spigot.

In FIGS. 22 and 23, two additional constructions for a spigot are shown, designated as spigot 160 in FIG. 22 and spigot 160A in FIG. 23. Spigot 160 in FIG. 22 has a spigot channel 161, annular flange 162 and a spigot inlet portion 164. The spigot 160 also provides an ozone channel 165 that communicates with spigot channel 161. Valving member 167 prevents the flow of ozone from flowline 130 to directly to water inlet opening 156. Rather, when ozone is being dispensed into channel 161, back pressure causes valving member 167 to close. The valving member 167 is pivotally attached to spigot 160 at pivot 168.

The valving member 167 is normally closed due to gravity and backpressure and opens when water is being dispensed as when valve 152 is opened. Valving member 167 can be partially open due to bouyancy. However, it will close after ozone begins to flow as shown by arrows 166. The spigot 160 provides the same dispensing portion that includes a valving member 152 and a valve outlet 151 as shown in FIG. 20. Those portions have been removed from FIG. 22 for purposes of clarity.

In FIG. 22, arrow 166 shows the flow of ozone from flowline 130 through fitting 163 to ozone channel 165. The ozone flowing in channel 165 reaches fitting 147 that is connected to diffuser 134. Ozone flows from flowline 130 to diffuser 134 and without the necessity of a second opening in reservoir wall 143. Arrow 169 schematically illustrates the opening and closing of valving member 167.

In FIG. 23, another spigot 160A is shown. The spigot 168 is a construction that can be used to modify an existing spigot because the spigot inlet portion 164A is a "retrofit" part. In FIG. 23, the existing spigot on a cooler/dispenser is milled to receive the retrofit spigot inlet portion 164A. The spigot inlet portion 164A provides water inlet opening 171 and ozone channel 170. The ozone channel 170 communicates with a fitting 173 that can be integrally formed with the spigot inlet portion 164A. Arrow 172 in FIG. 23 shows the path of water being dispensed when the valve 152 is opened and water flows from reservoir 141 to water inlet opening 171 and to spigot channel 161. When water is not being dispensed and ozone is to be transmitted via flowline 130, the valving member 167 closes because of gravity and back pressure. Ozone enters the channel 161 and also the ozone channel 170.

The following table lists the parts numbers and parts descriptions as used herein and in the drawings attached hereto.

PARTS LIST

| Part Number | Description |
|---|---|
| 10 | water dispenser |
| 11 | cabinet |
| 12 | lower end |
| 13 | upper end |
| 14 | cover |
| 15 | annular flange |
| 16 | gasket |
| 17 | opening |
| 18 | bottle |
| 19 | bottle neck |
| 20 | reservoir |
| 21 | interior |
| 22 | reservoir side wall |
| 23 | reservoir bottom wall |
| 24 | open top |
| 25 | water surface |
| 26 | spigot |
| 27 | spigot |
| 28 | refrigeration coil |
| 29 | compressor |
| 30 | flow line |
| 31 | flow line |
| 32 | heat exchanger |
| 33 | electrical line |
| 34 | plug |
| 35 | flow line |
| 36 | outlet port |
| 37 | diffuser |
| 37A | diffuser |
| 38 | air line |
| 39 | fitting |
| 40 | housing |
| 41 | electrical line |
| 42 | controller |
| 43 | plug |
| 44 | receptacle |
| 45 | flange |
| 46 | opening |
| 47 | lower end |
| 48 | upper end |
| 49 | opening |
| 50 | ozone generator |

-continued

PARTS LIST

| Part Number | Description |
|---|---|
| 51 | transformer |
| 52 | electrical line |
| 53 | motor |
| 54 | blower |
| 55 | air line |
| 56 | air inlet |
| 57 | ozone generator housing |
| 58 | lower housing section |
| 59 | upper housing section |
| 60 | flange |
| 61 | flange |
| 62 | gasket |
| 63 | bolted connection |
| 64 | internally threaded opening |
| 65 | arrow |
| 66 | arrow |
| 67 | bubble |
| 68 | foot |
| 69 | opening |
| 70 | angle |
| 71 | filter |
| 72 | porous body |
| 73 | inner surface |
| 74 | outer surface |
| 75 | hollow bore |
| 76 | non-porous coating |
| 77 | end portion |
| 78 | end portion |
| 79 | elbow fitting |
| 80 | body |
| 81 | leg |
| 82 | leg |
| 83 | coupling material |
| 84 | bore |
| 85 | bore |
| 86 | external threads |
| 87 | stab fitting |
| 88 | grinding tool |
| 89 | shaft |
| 90 | exposed face |
| 91 | arrow |
| 92 | bubble |
| 100 | water dispenser |
| 101 | cabinet |
| 102 | cover |
| 103 | annular flange |
| 104 | gasket |
| 105 | opening |
| 106 | bottle |
| 107 | neck |
| 108 | opening |
| 109 | reservoir |
| 110 | bottom |
| 111 | wall |
| 112 | outlet |
| 113 | channel |
| 114 | flow bore |
| 115 | spigot |
| 116 | valve |
| 117 | dispensing opening |
| 118 | spigot flow channel |
| 119 | first passage |
| 120 | second passage |
| 121 | tangent position |
| 122 | spiral arrow |
| 123 | diffuser |
| 124 | opening |
| 125 | O-ring |
| 126 | closure cap |
| 127 | internally threaded opening |
| 128 | fitting |
| 129 | fitting |
| 130 | ozone flowline |
| 131 | ozone flowline |
| 132 | ozone generator module |

-continued

PARTS LIST

| Part Number | Description |
|---|---|
| 133 | arrow |
| 134 | diffuser |
| 134A | diffuser |
| 135 | arrow |
| 136 | arrow |
| 137 | flowline |
| 138 | ozone generator |
| 139 | arrow |
| 140 | blower |
| 141 | reservoir |
| 142 | opening |
| 143 | wall |
| 144 | bottom |
| 145 | fitting |
| 146 | flowline |
| 146A | flowline portion |
| 146B | flowline portion |
| 147 | fitting |
| 148 | arrow |
| 150 | spigot |
| 151 | outlet |
| 152 | valve |
| 153 | spigot channel |
| 154 | annular flange |
| 155 | spigot inlet portion |
| 156 | water inlet opening |
| 157 | arrow |
| 160 | spigot |
| 160A | spigot |
| 161 | channel |
| 162 | annular flange |
| 163 | fitting |
| 164 | spigot inlet portion |
| 164A | spigot inlet portion |
| 165 | ozone channel |
| 166 | arrow |
| 167 | valving member |
| 168 | pivot |
| 169 | arrow |
| 170 | ozone channel |
| 171 | water inlet opening |
| 172 | arrow |
| 173 | fitting |

The foregoing embodiments are presented by way of example only; the scope of the present invention is to be limited only by the following claims.

What is claimed is:

1. A bottled water dispenser, comprising:
   a) a cabinet having upper and lower end portions;
   b) the upper end portion of the cabinet having a cover with an opening for receiving and holding a bottle of water to be dispensed;
   c) a bottle containing water to be dispensed, said bottle having a neck portion and a dispensing outlet portion;
   d) reservoir contained within the cabinet, the reservoir containing water with a water surface that communicates with the bottle neck during use and a diffuser for diffusing gas inside the
   e) one or more spigots on the cabinet for dispensing water from the reservoir;
   f) a channel that connects the reservoir to the spigot; and
   g) an ozone generator housing positioned next to the cabinet, said housing having an ozone generator inside the housing and air flow lines for transmitting air to and from the housing interior; and
   h) a flowline that simultaneously transmits ozone from the ozone generator to the channel and to the diffuser.

2. The bottled water dispenser of claim 1 wherein the channel has an inclined section.

3. The bottled water dispenser of claim 1 wherein the channel includes first and second intersecting sections.

4. A bottled water dispenser of claim 1 wherein the channel includes an inclined section that communicates with the reservoir.

5. A bottled water dispenser, comprising:
   a) a cabinet having upper and lower end portions;
   b) the upper end portion of the cabinet having a cover with an opening for receiving and holding a bottle of water to be dispensed;
   c) a bottle containing water to be dispensed, said bottle having a neck portion and a dispensing outlet portion;
   d) reservoir contained within the cabinet, the reservoir containing water with a water surface that communicates with the bottle neck during use;
   e) one or more spigots on the cabinet for dispensing water from the reservoir;
   f) a channel that connects the diffuser for emitting bubbles into the reservoir, said diffuser being disposed within the reservoir;
   g) an ozone generator housing positioned next to the cabinet, said housing having an ozone generator inside the housing and air flow lines for transmitting air to and from the housing interior;
   h) a flowline that transmits ozone from the ozone generator to the channel; and
   i) wherein the spigot has ports that receive ozone via the flowline.

6. The bottled water dispenser of claim 5 wherein the ports include a port having a diffuser.

7. The bottled water dispenser of claim 6 wherein the diffuser is removable.

8. A bottled water dispenser, comprising:
   a) a cabinet having upper and lower end portions;
   b) the upper end portion of the cabinet having a cover with an opening for receiving and holding a bottle of water to be dispensed;
   c) a bottle containing water to be dispensed, said bottle having a neck portion and a dispensing outlet portion;
   d) reservoir contained within the cabinet, the reservoir containing water with a water surface that communicates with the bottle neck during use;
   e) one or more spigots on the cabinet for dispensing water from the reservoir;
   f) a channel that connects the diffuser for emitting bubbles into the reservoir, said diffuser being disposed within the reservoir;
   g) an ozone generator housing positioned next to the cabinet, said housing having an ozone generator inside the housing and air flow lines for transmitting air to and from the housing interior;
   h) a flowline that transmits ozone from the ozone generator to the channel, The bottled water dispenser of claim 1 wherein the spigot has ports that receive ozone via the flowline; and
   i) a second flowline that communicates between a spigot and the reservoir.

9. The bottled water dispenser of claim 8 further comprising a tee fitting for transmitting ozone to the first and second flowlines.

10. A bottled water dispenser, comprising:
    a) a cabinet having upper and lower end portions and a spigot for dispensing water;

b) reservoir contained within the cabinet, the reservoir containing water;

c) a channel that transmits water from the reservoir to the spigot;

d) a diffuser for emitting bubbles into the reservoir;

e) an ozone generator module positioned next to the cabinet, said generator including a housing having an ozone generator inside the housing, and a blower for generating air flow; and f) a spigot sanitizing conduit that transmits ozone from the ozone generator module to the spigot and channel.

11. The bottled water dispenser of claim 10 wherein the channel has an inclined section.

12. The bottled water dispenser of claim 10 wherein the channel includes first and second intersecting sections.

13. The bottled water dispenser of claim 10 wherein the spigot has ports that receive ozone via the flowline.

14. The bottled water dispenser of claim 10 wherein the ports include a port having a diffuser.

15. The bottled water dispenser of claim 10 wherein the diffuser is removable.

16. The bottled water dispenser of claim 10 further comprising a flowline that communicates between a spigot channel and the reservoir.

17. The bottled water dispenser of claim 10 further comprising tee fitting for transmitting ozone to the first and second flowlines.

18. The bottled water dispenser of claim 10 wherein the channel includes an inclined section that communicates with the reservoir.

19. The bottled water dispenser of claim 10 wherein the conduit transmits ozone to sanitize the spigot, the spigot channel and the reservoir.

20. A method of sanitizing a bottled water dispenser having a cabinet with a dispensing spigot, a reservoir and a channel that flows water between the reservoir and the spigot, comprising the steps of:

a) generating ozone with an ozone generator that is positioned next to the cabinet;

b) collecting the generated ozone inside of an ozone generator housing;

c) providing an ozone diffuser inside the reservoir; and d) simultaneously transmitting ozone from the ozone generator housing to the channel.

21. The method of claim 20 further comprising the step of transmitting ozone that is in the channel to the reservoir.

22. The method of claim 20 wherein separate flowline sections communicate between the ozone generator and each of the reservoir, channel, and spigot and further comprising the step sanitizing the reservoir and spigot with ozone using the separate flowline sections.

23. The method of claim 20 wherein the flowlines include a return flowline that returns ozone from the spigot to the channel.

24. The method of claim 20 wherein the flowlines include a return flowline that returns ozone from the spigot to the reservoir.

25. The method of claim 20 further comprising transmitting ozone to two spaced apart ports on the spigot.

26. The method of claim 20 wherein in step "d" ozone is transmitted to the reservoir, channel and spigot.

27. The method of claim 26 wherein in step "d" there is a single flowline that enters the reservoir through a single opening for transmitting ozone to both the reservoir and the channel.

28. The method of claim 20 further comprising the step of transmitting ozone to the spigot.

29. A method of sanitizing a bottled water dispenser having a cabinet with a dispensing spigot, a reservoir and a channel that connects the spigot and reservoir, comprising the steps of:

a) generating ozone with an ozone generator that is positioned next to the cabinet;

b) collecting the generated ozone inside of an ozone generator housing;

c) providing an ozone diffuser inside the reservoir;

d) transmitting ozone from the ozone generator housing to at least the reservoir and the channel; and e) wherein the flowlines include a flowline that extends between the spigot and reservoir.

30. A method of sanitizing a bottled water dispenser having a cabinet with a dispensing spigot, a reservoir and a channel that flows water between the reservoir and the spigot, comprising the steps of:

a) generating ozone with an ozone generator that is positioned next to the cabinet;

b) collecting the generated ozone inside of an ozone generator housing;

c) providing an ozone diffuser inside the reservoir; and d) transmitting ozone from the ozone generator housing to the spigot.

31. The method of claim 30 further comprising transmitting ozone from the spigot to the channel.

32. The method of claim 30 further comprising transmitting ozone from the spigot to the reservoir.

33. The method of claim 30 further comprising transmitting ozone to two spaced apart ports on the spigot.

34. The method of claim 30 wherein in step "d" ozone is transmitted to the reservoir, channel and spigot.

35. The method of claim 30 wherein in step "d" there is a single flowline that enters the reservoir through a single opening for transmitting ozone to both the reservoir and the channel.

36. The method of claim 30 further comprising the step of transmitting ozone to the reservoir.

* * * * *